(12) United States Patent
Karma et al.

(10) Patent No.: US 8,543,181 B2
(45) Date of Patent: Sep. 24, 2013

(54) SENSOR HOLDER FOR MEDICAL SENSOR (75) Inventors: Heikki Sakari Karma, Porvoo (FI);
Jani Mikael Kauppi, Helsinki (FI);
Milvi Kristina Soosalu, Espoo (FI)

(73) Assignee: General Electric Company,
Schenectady, NY (US)

( * ) Notice: Subject to any disclaimer, the term of this patent is extended or adjusted under 35 U.S.C. 154(b) by 422 days.

(21) Appl. No.: 12/898,789

(22) Filed: Oct. 6, 2010

(65) Prior Publication Data
US 2011/0124995 A1     May 26, 2011

(30) Foreign Application Priority Data

Nov. 26, 2009   (EP) ..................................... 09177134

(51) Int. Cl.
*A61B 5/1455*     (2006.01)
(52) U.S. Cl.
USPC ......................................... 600/344; 600/340

(58) Field of Classification Search
USPC .......................... 600/310, 322, 323, 340, 344
See application file for complete search history.

(56) References Cited

U.S. PATENT DOCUMENTS

| | | | |
|---|---|---|---|
| 4,825,872 A | 5/1989 | Tan et al. | |
| 5,337,744 A | 8/1994 | Branigan | |
| 5,413,102 A | 5/1995 | Schmidt et al. | |
| 6,505,061 B2 | 1/2003 | Larson | |
| 7,359,742 B2 | 4/2008 | Maser et al. | |
| 7,486,979 B2 | 2/2009 | Matlock | |
| 2006/0106294 A1 | 5/2006 | Maser et al. | |
| 2007/0032708 A1 | 2/2007 | Eghbal et al. | |

FOREIGN PATENT DOCUMENTS

DE        202005017567 U1    4/2007

*Primary Examiner* — Eric Winakur
(74) *Attorney, Agent, or Firm* — Global Patent Operation; Marc A. Vivenzio (57) ABSTRACT

A sensor holder for a medical sensor. The sensor holder includes a housing surrounding a hollow for a subject appendage, the housing having a first channel for a gas volume following the hollow, a first aperture, a second aperture and a third aperture for a ventilation of the gas volume of the first channel.

19 Claims, 4 Drawing Sheets

SENSOR HOLDER FOR MEDICAL SENSOR

BACKGROUND OF THE INVENTION

1. Field of the Invention

This disclosure relates generally to a sensor holder for a medical sensor.

2. Description of Related Art

Information on the amount of oxygen within blood or more preferably a blood flow is desirable in many instances. This is often characterized as the oxygen content or oxygen saturation of the blood. Oximeters are able to provide this type of information and are generally well known in the art. Patient data that is used by the oximeter to determine the oxygen content/saturation is monitored/measured by an oximeter sensor that operatively interfaces with the oximeter.

Oximeter sensors typically employ a pair of light sources that emit light at different wavelengths, as well as one or more optical detectors. Electrical signals are provided by the oximeter to the oximeter sensor to operate the light sources in a predetermined manner (e.g., each light source is "pulsed" in accordance with a predetermined pattern). Light from each of the light sources will either be absorbed by the blood or will pass entirely through the patient's tissue and blood for receipt by the detector(s). Electrical signals from the detector(s) are provided back to the oximeter. Information on how the light sources are being operated, the wavelengths of these two light sources, and the amount of light, which passes through the blood to the detector(s) are all used by the oximeter to calculate the oxygen content/saturation of the blood. This information will then typically be displayed for review by appropriate personnel.

Various factors contribute to the overall success of a given oximeter sensor holder. One is its comfort when positioned on the relevant body part. It would be desirable to have an oximeter sensor holder that provided at least a certain degree of a patient comfort and would not cause breakdown of the patient's skin when worn for long periods of time. Enhanced patient comfort can be realized by things such as the size, shape, and weight of the oximeter sensor holder, as well as having the oximeter sensor holder interface with the patient so as to at least reduce the potential for the development of "pressure points." Uneven distribution of the forces being exerted on the patient by the oximeter sensor holder can contribute to the development of undesired soreness and possibly pressure necrosis on the patient's skin surface.

Another well-known discomfort is the sweating of the relevant body part. More closed the sensor holder structure is more sweating it can cause and thus at least the patients that are conscious tend to cool the finger themselves that causes measurement stops. Also excessive sweating increases the need for cleaning.

Being a reusable oximeter sensor, one of the biggest challenge together with the comfort, is the durability of the sensor holder. The known mechanical failure in the oximeter sensor holders is the wire breakage that may occur when the cable is repeatedly bent relative to the sensor holder. If the oximeter sensor holder is designed to separate the single wires inside the cable right after the point where the flex relief integrates to the sensor holder, there will be a point of mechanical discontinuance that may lead to the described breakage.

There are a number of competing design considerations for oximeter sensor holders. First, the sensor holders should have the ability to achieve a reliable interface between the emitter and detector in the sensor holder and the patient's skin. Second, the oximeter sensor holder should be adapted for ready application and removal from the patient with a minimal amount of pair or discomfort for the patient. Finally, the oximeter sensor holder should provide a gentle interface with the patient's skin.

There are various means for holding the emitter(s)/detector in contact to a patient's tissue; however, two common types are flexible and clip-type sensor holders. Many currently available clip-type sensor holders have a hard shell, which has a high profile and is maintained on the finger by the action of a spring. Since excess pressure on the finger can dampen or eliminate the pulsation in the blood supply to the finger, these springs are intentionally relatively weak. The result of this compromise is that the spring-held sensor holders readily fall off the finger. It is desirable for a finger sensor holder to be retained on the finger with only slight pressure, while at the same time being immune to easy dislocation. Also accommodation on the different sizes of the finger is challenging to achieve with a sensor holder having hinge(s). Flexible sensor holders may simply comprise an elastic holder onto which the emitter(s)/detector are mounted for placement about a patient appendage.

There are known sensor holder designs that are designed to provide an evenly distributed pressure around the finger. However no sensor holder has been designed equal to the shape of a human finger. The ones closest to finger shape design do not distribute pressure evenly around the finger. Also majority of the known sensor holder designs are closed structures, so that only the proximal and distal ends are open, causing easily sweating and moisture between the sensor holder and finger. The few sensor holder designs that introduce holes or openings on the sensor holder between both ends have a high possibility to create pressure points on the edges of the openings that lay against the finger. Also the openings are not cooling the skin elsewhere, than just on the opening area as there are no air circulation between those openings and proximal/distal ends.

BRIEF SUMMARY OF THE INVENTION

The above-mentioned shortcomings, disadvantages and problems are addressed herein which will be understood by reading and understanding the following specification.

In an embodiment, a sensor holder for a medical sensor includes a housing configured to surround a hollow for a subject appendage, the housing having a first channel for a gas volume following the hollow, a first aperture, a second aperture and a third aperture for a ventilation of the gas volume of the first channel.

In another embodiment, a sensor holder for a medical sensor includes a housing configured to surround a hollow for a subject appendage, the housing having a first channel for a gas volume following the hollow, a first aperture, a second aperture and a third aperture for a ventilation of the gas volume of the first channel. The first aperture and second aperture are configured to locate on opposite ends of the first channel, the third aperture being therebetween locating on such an edge of the first channel which is apart from a border between the hollow and the first channel.

In yet another embodiment, a sensor holder for a medical sensor includes a housing configured to surround a hollow for a subject appendage, the housing having a first channel for a gas volume following the hollow, a first aperture, a second aperture and a third aperture for a ventilation of the gas volume of the first channel, and the housing also having a second channel for a gas volume following the hollow, a fourth aperture, a fifth aperture and a sixth aperture for a ventilation of the gas volume of the second channel.

Various other features, objects, and advantages of the invention will be made apparent to those skilled in art from the accompanying drawings and detailed description thereof.

BRIEF DESCRIPTION OF THE DRAWINGS

Reference is now made briefly to the accompanying drawings, in which.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
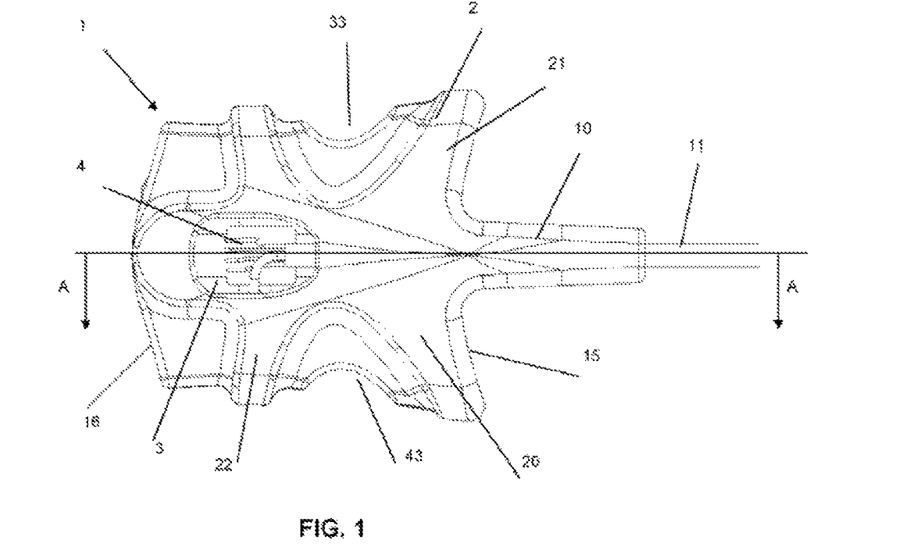
FIG. 1 is a top view of a sensor holder in accordance with an embodiment.
Figure 2:
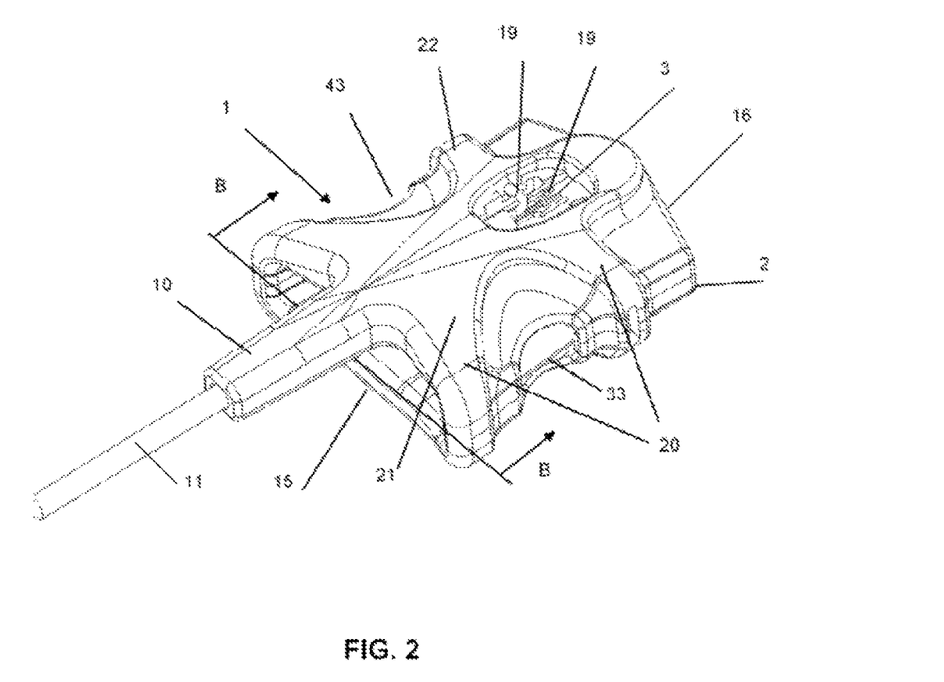
FIG. 2 is a top perspective view of a sensor holder of FIG. 1.
Figure 3:
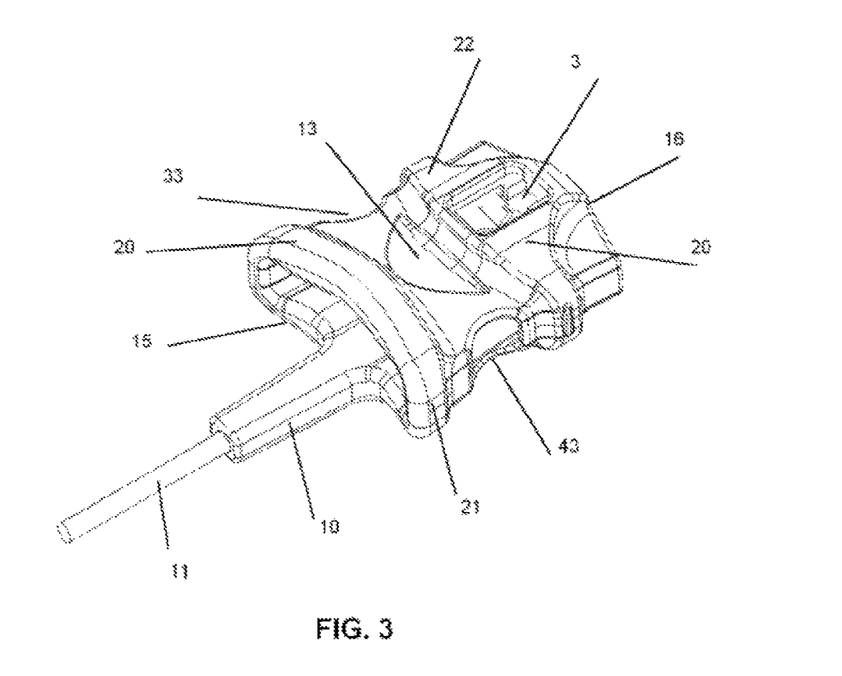
FIG. 3 is a bottom perspective view of the sensor holder of FIG. 1.

FIGS. 1, 2 and 3 show a sensor holder 1 from different sides. The sensor holder 1 having at least one place 3 such as a recess for a medical sensor 4 shown in FIG. 4 can be positioned in a subject's appendage such as a finger or toe to measure blood or tissue constituents and/or pulse rate of the subject. Blood constituents are for example an amount of oxygen, methemoglobin, carboxyhemoglobin. A typical combination of the sensor holder 1 and the sensor 4 is frequently used with a pulse oximeter to measure oxygen saturation. The sensor holder 1 comprises a housing 2 which may preferably be made of a resilient molded polymer such as silicon and the housing can be either overmolded around the sensor 4 including electrical components or a separately molded component that will be furnished with the sensor needed for the measurement. Thus the sensor 4 may form an integral structure with the sensor holder 1 or the sensor holder can be a separate part from the sensor.

Figure 4:
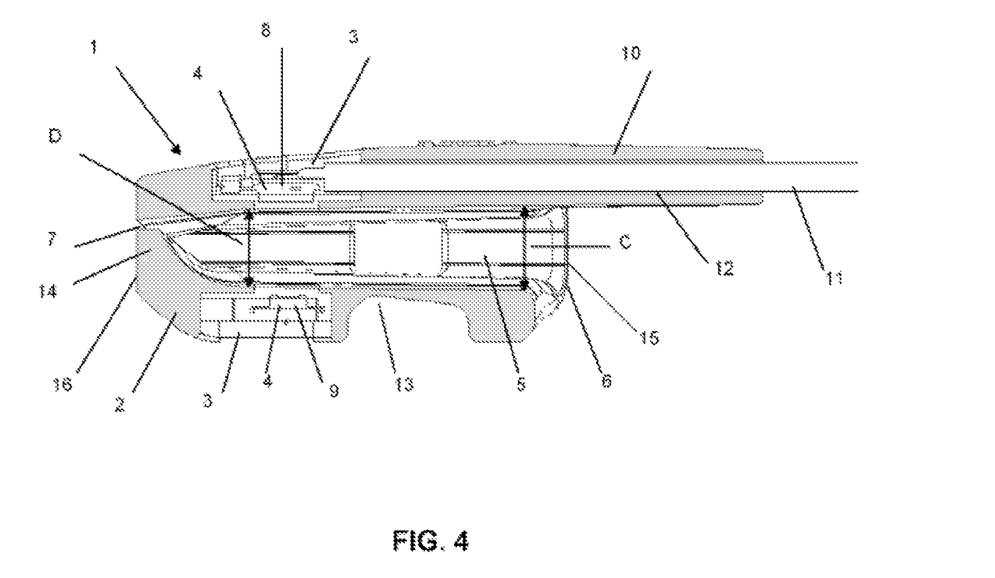
FIG. 4 is a cross section of the sensor holder of FIG. 1 taken along lines A-A.

The housing 2 surrounds a hollow 5 having a first end 6 and a second end 7 as can be seen in FIG. 4, which is a cross section along a line A-A of FIG. 1. The first end 6 of the hollow 5 is open and designed so that the appendage can be inserted through this first end 6 to the hollow 5 extending at least to the place 3 for the medical sensor 4. In this embodiment the sensor 4 comprises one or more emitters 8 for emitting one or more wavelengths depending on the constituent or constituents needed to measure and one or more detectors 9 for detecting emitted wavelengths transmitted the tissue whereupon the appendage should extend in the hollow 5 at least until the sensor 4 so that the wavelength emitted by the emitter 8 is able to transmit the tissue and reach the detector 9 opposite the emitter 8. In the embodiment shown in FIG. 4 a tip of the appendage should be positioned between the emitter 8 and the detector 9. The second end 7 of the hollow 5 could be closed or could be open or partly open as shown in FIG. 4 preventing from pushing the appendage through the second end 7 but allowing a tip of a nail to penetrate the second end 7. In this latter alternative the second end 7 comprises a stopper 14 to find an optimal position and correct penetration depth for the appendage in relation to a location of the sensor 4.

FIGS. 1, 2, 3 and 4 show a flex relief structure 10 for a cable 11 connectable between the sensor 4 and a monitor (not shown in Figures) for guiding a function of the sensor 4 and determining measurement results based on signals received from the sensor 4. The flex relief structure can be part of the housing 2 that carries the flex strength from the cable 11 to the sensor 4. The housing 2 includes a canal 12 as shown in FIG. 4. A cross section of the canal is small enough to press the cable 11 tightly. It is desirable to allow the canal 12 to extend in the housing 2 more than half of a length of that housing between its proximal end 15 and distal end 16 forming a strong fixing between the housing 2 and the cable 11. The canal 12 and the flex relief structure 10 can further extend outside the housing 2 going beyond the proximal end 15 or in some other embodiment the distal end 16 of the housing 2.

The jacketed cable 11 extends unpeeled inside the canal 12 towards the place 3 for the medical sensor 4. Signal wires 19 as shown in FIG. 2 inside the cable 11 separate in the place 3 for the medical sensor 4 in order to maintain the durability of the raw cable inside the flex relief structure 10. The separation of the signal wires 19 is needed to make the connections to the sensor 4 comprising sensor parts such as the emitter 8 and the detector 9 on opposite sides of the housing 2 surrounding the hollow 5. FIG. 2 illustrates the counter component such as the detector 9 of the sensor 4 that is also placed on the place 3 for the medical sensor 4 which is in this embodiment on opposite side of the emitter 8 of the sensor. A needed amount of signal wires 19 are routed to this place 3 for the medical sensor 4 and connected to the detector 9 in this case.

A wireless system (not shown in Figures) is also possible meaning that the flex relief structure 10 including the canal 12 and the cable 11 are not needed and can be replaced by a signal receiver and transmitter communicating wirelessly with the monitor. This kind of wireless system may be equipped with a small energy source such as a battery.

The housing 2 has advantageously as shown in FIGS. 2 and 3 one integral zone 20 offsetting other surfaces of the housing 2 that will cover the appendage. This integral zone 20 includes a substantially rigid edge 21 on the proximal end 15 resisting the stresses during the appendage penetration inside the housing 2 and a supporting ring 22 on the level of the place 3 for the medical sensor 4. The supporting ring 22 is hollow to form a path for the signal wires 19 to the place 3 for the medical sensor 4 which locates in this embodiment on opposite side of the emitter 8 of the sensor 4. Further the housing 2 has a thinning 13 between the place 3 for the medical sensor 4 or the supporting ring 22 and the rigid edge 21 of the proximal end 15 to facilitate the bending of the sensor and which thinning 13 is making the housing 2 thinner than those other parts of the housing between the supporting ring 22 and the rigid edge 21. This thinning 13 is in FIG. 3 embodiment on the surface of the housing 2 meant to press when bending the appendage.

Figure 5:
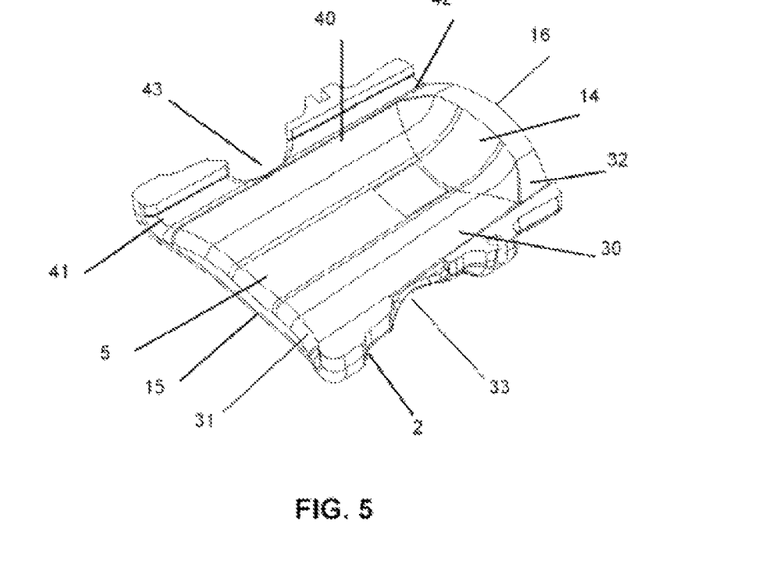
FIG. 5 is a cross section of the sensor holder of FIG. 2 taken along lines B-B.
Figure 6:
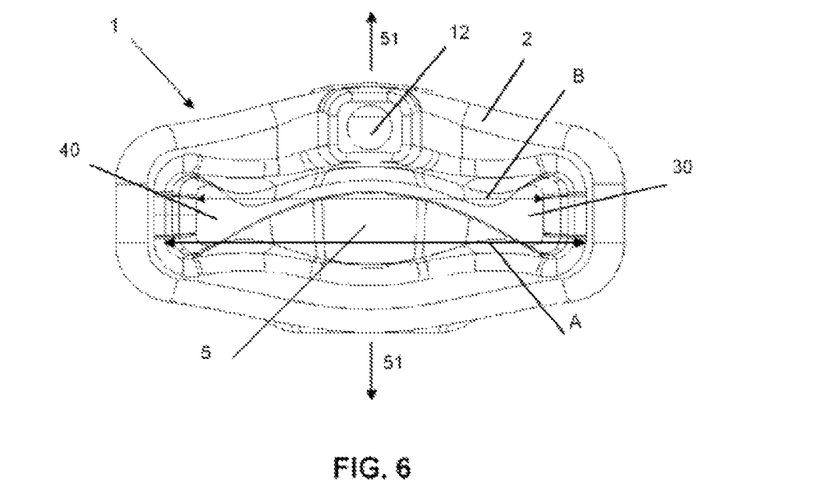
FIG. 6 is a proximal end view of the sensor holder of FIG. 1.

FIG. 5 shows a cross section of the sensor holder 1 of FIG. 2 taken along lines B-B and FIG. 6 shows a view of the proximal end of the sensor holder 1 of FIG. 1. The housing 2 of the sensor holder comprises a first channel 30 for a gas volume following the hollow 5 visible also in FIG. 4. The first channel 30, which is bordering the hollow 5, allows a ventilation of this hollow and the appendage when inserted into the hollow. The border between the first channel 30 and the hollow 5 is without a solid edge in which case this border can be only partly open allowing, however, the gas volume of the first channel to be in contact with an inside of the hollow or the appendage inserted in the hollow. The solid edge can for instance be just enough perforated. Or the border between the first channel 30 and the hollow 5 is preferably without any edge at all. This first channel may extend from the proximal end 15 of the housing 2 to the distal end 16 of the housing 2. For the ventilation as shown in FIG. 5 there is arranged at least three apertures. A first aperture 31 and a second aperture 32 allow ventilation between the first channel 30 and outside the housing 2. The ventilation is based on a gas flow or gas exchange between a surrounding of the sensor holder 1 and the first channel 30. The first aperture 31 and the second aperture 32 may locate on opposite ends of the first channel 30 in which case the first aperture 31 can locate in the proximal end 15 of the housing 2 and the second aperture 32 in the distal end 16 of the housing 2. Also there is a third aperture 33 locating between the opposite ends of the first channel 30, typically midway the opposite ends, improving the ventilation of the first channel 30. Between opposite ends there can be additional apertures, too. The shape and size of the apertures can vary, as well as the position. The improved ventilation may cool the appendage and consequently reduce sweating, which is a typical problem when using conventional sensor holders. This further helps to avoid moving the appendage reducing artefacts.

The housing 2 of the sensor holder 1 may also comprise a second channel 40 for a gas volume as shown in FIGS. 5 and 6 following the hollow 5 visible in FIG. 4, too. The second channel 40 is bordering the hollow 5 allowing its ventilation as well as the ventilation of the appendage when inserted into the hollow 5. The second channel 40 can be similar to the first channel 30, which was discussed hereinbefore. Also the border between the second channel 40 and the hollow 5 is without a solid edge in which case this border can be only partly open allowing, however, the gas volume of the second channel to be in contact with an inside of the hollow 5 or the appendage inserted in the hollow. The solid edge can for instance be just enough perforated. Or the border between the second channel 30 and the hollow 5 is preferably without any edge at all. Further this second channel may extend from the proximal end 15 of the housing 2 to the distal end 16 of the housing 2. For the ventilation there is arranged at least three apertures. A fourth aperture 41 and a fifth aperture 42 allow ventilation between the second channel 40 and outside the housing 2. The ventilation is based on a gas flow or gas exchange between a surrounding of the sensor holder 1 and the second channel 40. The fourth aperture 41 and the fifth aperture 42 may locate on opposite ends of the second channel 30 in which case the fourth aperture 41 can locate in the proximal end 15 of the housing 2 and the fifth aperture in the distal end 16 of the housing 2. Also there is a sixth aperture 43 locating between the opposite ends of the second channel 40, typically midway the opposite ends, improving the ventilation. Between opposite ends there can be additional apertures, too. The shape and size of the apertures can vary, as well as the position. The improved ventilation may also cool the appendage and consequently reduce sweating just as discussed with the first channel.

The first channel 30 and the second channel 40 are at a distance of each other as shown in FIGS. 5 and 6, but they are bordering the hollow 5. When the appendage is positioned in the hollow 5, the sides of the appendage are without a contact with the housing 2. The first channel 30 and the second channel 40 can locate on different sides of the hollow 5, typically on opposite sides, in which case the first channel and the second channel take care of the ventilation of both sides of the appendage. The first channel 30 is advantageously substantially parallel with the second channel 40, which means that the first and second channels are substantially parallel with the appendage when the appendage is inserted into the hollow 5. Further the first channel 30 and the second channel 40 can be straight following the hollow 5, which can also be straight. In case the hollow should follow a shape of the appendage the first and second channel can together with the hollow be substantially straight. Naturally it is possible to design the first and second channels in a way that they differ from the substantially straight design.

The third aperture 33 may locate on such an edge of the first channel 30, which is apart from the border between the hollow 5 and the first channel 30. Preferably the third aperture 33 is on an opposite edge of the first channel in proportion to the common border of the hollow 5 and the first channel 30 without a contact to the appendage to avoid pressure points on the skin. The third aperture 33 may be substantially perpendicular to a longitudinal axis of the hollow 5. In preferred embodiment the third aperture 33 is between the supporting ring 22 and the rigid edge 21 of the proximal end 15. This kind of structure reduces an unpleasant feeling which is the fact in case edges of the aperture press against the appendage.

Similarly the sixth aperture 43 may locate on such an edge of the second channel 40, which is apart from the border between the hollow 5 and the second channel 40. Preferably the sixth aperture 43 is on an opposite edge of the second channel 40 in proportion to the common border of the hollow 5 and the second channel 40 without a contact to the appendage to avoid pressure points on the skin. Also the sixth aperture 43 may be perpendicular or substantially perpendicular to a longitudinal axis of the hollow 5. In preferred embodiments the sixth aperture 43 is between the supporting ring 22 and the rigid edge 21 of the proximal end 15.

Figure 7:
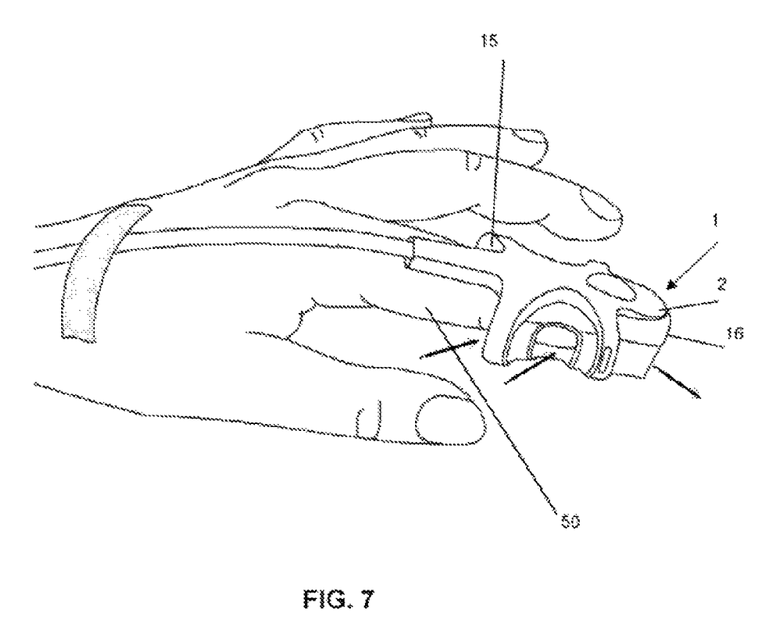
FIG. 7 shows a ventilation of the sensor holder of FIG. 1 when an appendage of a subject is in place.

FIG. 7 shows the sensor holder 1 when the appendage 50 is inserted into the hollow 5. Also this Figure shows how the design allows the air flow or gas exchange between the proximal end 15 and the distal end of the housing 2 via the first aperture 31, second aperture 32 and third aperture 33. Arrows 51 in FIG. 6 show the expansion of the housing 2 when used with different sizes of appendages. The housing 2 maintains its finger shaped design when stretched.

Figure 8:
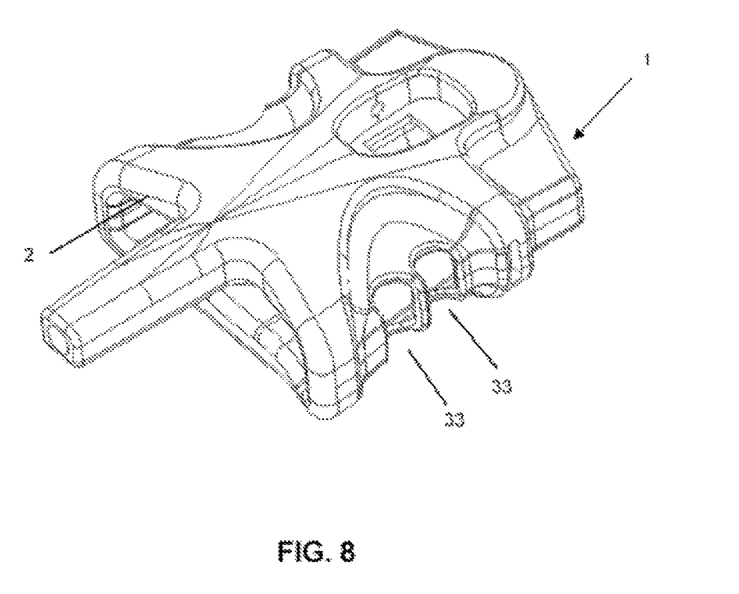
FIG. 8 is a perspective top view of a sensor holder in accordance with another embodiment.

A cross-sectional area of the aperture locating between the first aperture 31 and second aperture 32 such as the third aperture 33 of the first channel 30 and correspondingly the aperture locating between the fourth aperture 41 and fifth aperture 42 which are on the opposite ends of the second channel 40 such as the sixth aperture 43 should be at least 32 $mm^2$, more specifically at least 62 $mm^2$ or even more specifically at least 70 $mm^2$. It should be noted that the third and the sixth aperture can be divided into several apertures such as group of apertures as shown FIG. 8, but the common cross-sectional area of the several third or sixth apertures can be same as the single aperture.

Instead of two separate channels such as the first channel 30 and the second channel 40 taking care of the ventilation of both sides of the hollow 5 or the appendage there may be one extended channel, which may be the first channel 30 extended to go around from one side to another side of the hollow 5 following the hollow. For example the channel can go around the second end 7 of the hollow 5. Then the first aperture 31 and the second aperture 32 can locate on proximal end 15 of the housing 2, but if the channel is arranged to go around the first end 6 of the hollow 5, then the first aperture 31 and the second aperture 32 can locate on the distal end 16 of the housing. Also in this extended channel case it is desirable to have at least three apertures in the channel, the first aperture 31 and the second aperture 32 locating on opposite ends of the first channel 30 when the third aperture 33 locating between the opposite ends of the first channel 30 as discussed hereinbefore. Inasmuch as the channel is extended there may be a reason to add between the first aperture and the second aperture the fourth aperture. To make the ventilation more effective the fifth aperture is desired, but adding the sixth aperture to the extended first channel would make it even more effective. Also in this case it is advantageous to have at least two such apertures between the opposing ends of the channel having a cross-sectional area determined hereinbefore for the third and sixth aperture.

FIG. 6 being a view of the proximal end of the sensor holder 1 of FIG. 1 shows an inner width W1 of the housing 2. The inner width W1 including the width of the first channel 30, the second channel 40 and the hollow 5 therebetween at the proximal end 15 of the housing 2 is at least 30.5 mm, more specifically at least 33 mm or even more specifically 34.7 mm at maximum. An inner width W2 of the housing 2 when the inner width includes the first channel 30, the second channel 40 and the hollow 5 therebetween at the distal end 16 of the housing 2 is at least 25 mm, more specifically at least 27 mm or even more specifically 29.5 mm at maximum. These inner width dimensions are especially for the sensor holder designed for adults.

As shown in FIG. 4 an inner height H1 of the hollow 5 at the proximal end 15 of the housing 2 is at least 7.5 mm, more specifically at least 8.2 mm or even more specifically 8.9 mm at maximum. An inner height H2 of the hollow 5 at distal end 16 of the housing 2 where the place 3 for the medical sensor 4 locates is at least 7 mm, more specifically at least 7.5 mm or even more specifically 8.3 mm at maximum. These width and height dimensions enable evenly distributed pressure on the appendage. As the dimensions prove a cross-sectional area of the hollow 5 is reducing from the proximal end 15 towards the distal end 16 making it conical. Also these height dimensions are especially for the sensor holder designed for adults.

An advantage of the sensor holder 1 discussed hereinbefore is its reusability which securely attaches to a subject's appendage while reducing any interference with a blood circulation. The sensor holder can accommodate on various sizes of appendages and is resistant to a contamination. Due to nonexistent nooks and crannies on the hollow surface between the appendage and the sensor holder 1 the air flow or gas exchange is allowed reducing a movement relative to the appendage. The sensor holder is durable and configured for ease of assembly. The sensor holder 1 keeps the sensor 4 in the form that allows an evenly distributed pressure around the appendage, regardless of the finger size, due to the ability of the movement between sensor parts such as the emitter 8 and the detector 9. Also an advantage is that the inner shape of the hollow 5 of the sensor holder 1 maintains its appendage like design when stretched.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A sensor holder for a medical sensor comprising:
   a housing;
   a hollow defined by said housing and configured to receive a subject appendage;
   said housing defining a first channel for a gas volume adjacent said hollow, said housing further defining each of a first aperture, a second aperture and a third aperture in communication with said first channel for a ventilation of the gas volume of said first channel.

2. The sensor holder according to claim 1, wherein said first aperture and second aperture are configured to locate on opposite ends said first channel, said third aperture being therebetween and said first, second and third apertures are configured to allow airflow outside said housing to improve cooling of the appendage when the appendage is in place inside the hollow.

3. The sensor holder according to claim 2, wherein said third aperture between said opposite ends of said first channel is configured to locate on an edge of said first channel which is apart from a border between said hollow and said first channel.

4. The sensor holder according to claim 1, wherein said housing having a proximal end and a distal end comprises a second channel for a gas volume adjacent said hollow, a fourth aperture, a fifth aperture and a sixth aperture for a ventilation of the gas volume of said second channel, said fourth and fifth apertures being on opposite ends of said second channel, said sixth aperture being therebetween.

5. The sensor holder according to claim 4, wherein said first channel and second channel are on different sides of the hollow, typically on opposite sides of said hollow.

6. The sensor holder according to claim 4, wherein said third aperture and sixth aperture are perpendicular to said hollow and a bending direction of the appendage when the appendage is in place inside said hollow.

7. The sensor holder according to claim 5, wherein said first channel is substantially parallel with said second channel and which first and second channels are substantially parallel with the appendage when the appendage is inserted into said hollow.

8. The sensor holder according to claim 4, wherein said sixth aperture between said opposite ends of said second channel is configured to locate on an edge of said second channel which is apart from a border between said hollow and said second channel.

9. The sensor holder according to claim 4, wherein a cross-sectional area of at least one of said third aperture and sixth aperture is at least 32 mm$^2$.

10. The sensor holder according to claim 4, wherein an inner width W1 of the housing including a width of the first channel, the second channel and the hollow therebetween at the proximal end of said housing is at least 30.5 mm.

11. The sensor holder according to claim 4, wherein an inner width W2 of the housing including a width of the first channel, the second channel and the hollow therebetween at the distal end of said housing is at least 25 mm.

12. The sensor holder according to claim 1, wherein said housing comprises at least one place for a medical sensor.

13. The sensor holder according to claim 1, wherein said sensor comprising at least one emitter and at least one detector is configured to form an integral structure with said sensor holder or said sensor holder is a separate part from said sensor.

14. The sensor holder according to claim 1, wherein an inner height H1 of the hollow at a proximal end of the housing is at least 7.5 mm, and an inner height H2 of the hollow at a distal end of the housing where the medical sensor is placed is at least 7 mm.

15. The sensor holder according to claim 1, wherein said housing comprises a canal for a cable connectable to said sensor and which canal extends in said housing more than half of a length of said housing forming a strong fixing between said housing and said cable.

16. A sensor holder for a medical sensor comprising:
a housing;
a hollow defined by said housing and configured to receive a subject appendage;
said housing defining a first channel for a gas volume adjacent said hollow, a first aperture, a second aperture and a third aperture in communication with said first channel for a ventilation of the gas volume of said first channel,
wherein said first aperture and second aperture are configured to locate on opposite ends of said first channel, said third aperture being therebetween locating on such an edge of said first channel which is apart from a border between said hollow and said first channel.

17. The sensor holder according to claim 16, wherein a cross-sectional area of said third aperture is at least 32 mm².

18. The sensor holder according to claim 16, wherein said sensor comprising at least one emitter and at least one detector is configured to form an integral structure with said sensor holder.

19. A sensor holder for a medical sensor comprising:
a housing;
a hollow defined by said housing and configured to receive a subject appendage;
said housing defining a first channel for a gas volume adjacent said hollow, and each of a first aperture, a second aperture and a third aperture for a ventilation of the gas volume of said first channel; and
said housing further defining a second channel for a gas volume adjacent said hollow, the first and second channels being on opposite sides of said hollow, said housing further defining each of a fourth aperture, a fifth aperture and a sixth aperture for a ventilation of the gas volume of said second channel.

* * * * *

UNITED STATES PATENT AND TRADEMARK OFFICE
CERTIFICATE OF CORRECTION

| | | |
|---|---|---|
| PATENT NO. | : 8,543,181 B2 | Page 1 of 1 |
| APPLICATION NO. | : 12/898789 | |
| DATED | : September 24, 2013 | |
| INVENTOR(S) | : Karma et al. | |

It is certified that error appears in the above-identified patent and that said Letters Patent is hereby corrected as shown below:

In the Specification

In Column 2, Line 1, delete "pair" and insert -- pain --, therefor.

In Column 5, Line 40, delete "second channel 30" and insert -- second channel 40 --, therefor.

In Column 5, Lines 49-50, delete "second channel 30" and insert -- second channel 40 --, therefor.

Signed and Sealed this
Seventeenth Day of December, 2013

Margaret A. Focarino
*Commissioner for Patents of the United States Patent and Trademark Office*